(12) United States Patent
Fukazawa

(10) Patent No.: US 8,223,328 B2
(45) Date of Patent: Jul. 17, 2012

(54) SURFACE INSPECTING APPARATUS AND SURFACE INSPECTING METHOD

(75) Inventor: Kazuhiko Fukazawa, Kamakura (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 13/241,029

(22) Filed: Sep. 22, 2011

(65) Prior Publication Data

US 2012/0069335 A1    Mar. 22, 2012

Related U.S. Application Data

(63) Continuation of application No. 12/852,015, filed on Aug. 6, 2010, now abandoned, which is a continuation of application No. PCT/JP2009/051962, filed on Feb. 5, 2009.

(30) Foreign Application Priority Data

Feb. 6, 2008    (JP) .................................. 2008-026759

(51) Int. Cl.
*G01N 21/00* (2006.01)
(52) U.S. Cl. .................... 356/237.2; 356/237.5
(58) Field of Classification Search ..... 356/237.1–237.5
See application file for complete search history.

(56) References Cited

U.S. PATENT DOCUMENTS 6,621,568 B1    9/2003    Yonezawa

FOREIGN PATENT DOCUMENTS

| DE | 600 24 924 T2 | 8/2006 |
| EP | 1 065 499 A2 | 1/2001 |
| EP | 1 065 499 A3 | 1/2001 |
| JP | 1-147349 A | 6/1989 |
| JP | 10-232122 A | 9/1998 |
| JP | 2001-13085 A | 1/2001 |
| JP | 2005-147691 A | 6/2005 |
| JP | 2007-309874 | 11/2007 |
| JP | 2007-327796 A | 12/2007 |
| JP | 2008-8777 A | 1/2008 |

*Primary Examiner* — Michael P Stafira
(74) *Attorney, Agent, or Firm* — Miles & Stockbridge P.C.

(57) ABSTRACT

A surface inspecting apparatus includes an illumination optical system irradiating linearly polarized light to a wafer surface under a plurality of inspection conditions; an imaging optical system capturing an image of the wafer formed by polarization components having an oscillation direction different from that of the linearly polarized light as part of reflected light from the wafer surface irradiated by the linearly polarized light under the plurality of inspection conditions; and an image-processing apparatus for extracting for individual pixels an image having the smallest signal intensity from among images of the wafer captured under the plurality of inspection conditions by the imaging optical system, and for inspecting for the presence of defects in a repeated pattern of the wafer based on an inspection image of the wafer generated by connecting each of the extracted pixels.

15 Claims, 8 Drawing Sheets

SURFACE INSPECTING APPARATUS AND SURFACE INSPECTING METHOD

CROSS-REFERENCE TO RELATED APPLICATION

This is a continuation of application Ser. No. 12/852,015 filed Aug. 6, 2010 now abandoned, which is a continuation of PCT International Application No. PCT/JP2009/051962, filed on Feb. 5, 2009, which is hereby incorporated by reference. This application also claims the benefit of Japanese Patent Application No. 2008-026759, filed in Japan on Feb. 6, 2008, which is hereby incorporated by reference.

TECHNICAL FIELD

The present invention relates to a surface inspecting apparatus and surface inspecting method for inspecting the surface of a semiconductor wafer, liquid crystal substrate, or the like.

TECHNICAL BACKGROUND

In the process of manufacturing a semiconductor circuit element or liquid crystal display element, repeated patterns (wiring patterns and other line-and-space patterns) formed on the surface of the semiconductor wafer or liquid crystal substrate (hereinafter referred to generically as "the substrate") are inspected for defects. In an automated surface inspecting apparatus, the substrate is placed on a tiltable stage, illuminating light (non-polarized light) for used in performing an inspection is irradiated onto the surface of the substrate, an image of the substrate is acquired based on diffracted light (e.g., $1^{st}$-order diffracted light) generated from the repeated pattern on the substrate, and the locations of defects in the repeated pattern are identified based on the differences between lightness and darkness (contrast) in the image (see, e.g., Patent Document 1). In such a surface inspecting apparatus, adjusting the tilt of the stage makes it possible to inspect for defects in a repeated pattern having a different repetition pitch on the substrate.

Techniques for inspecting a repeated pattern formed on the surface of a substrate include inspection using diffracted light such as described above (referred to hereinafter as diffraction inspection), using direct reflection light, utilizing changes in polarization state due to structural birefringence of the pattern (hereinafter referred to as PER inspection), and other techniques. These inspection methods enable resist application defects, line width defects based on defocusing or dose shift of an exposure apparatus, and other defects to be detected at high speed with high accuracy.

As the line width of the repeated pattern decreases, the wavelength of the illumination used for diffraction inspection must be shortened, and in repeated patterns having a line width of 45 nm or less, there is no illumination light source that is optimal for diffraction inspection, and the inspection is performed by PER inspection. In repeated patterns having a line width of 45 nm or less, changes in the shape of the pattern on the order of 1 nm must be detected, and high sensitivity is required to detect changes in the shape of the pattern.

Patent Document 1: Japanese Laid-open Patent Publication No. H10-232122

DISCLOSURE OF THE INVENTION

Problems to be Solved by the Invention

Although three types of parameters such as the illumination wavelength, for example, are known as conditions that enhance the sensitivity of detection in PER inspection, it is difficult to derive the optimum inspection conditions by combining these three types of parameters, and there is also no method of determining the appropriateness of inspection conditions. Performing all inspections under a plurality of inspection conditions with varying parameters is also problematic because of the long time required, and false positives occur in defect detection.

The present invention was developed in view of such problems, and an object of the present invention is to provide a surface inspection apparatus and surface inspection method capable of inspection at high speed with high accuracy.

Means to Solve the Problems

The surface inspection apparatus of the present invention for achieving the abovementioned objects comprises an illumination unit for irradiating linearly polarized light onto a surface of an inspected substrate having a predetermined repeating pattern; an imaging unit for capturing an image of the inspected substrate formed by polarization components having an oscillation direction that is different from that of the linearly polarized light as part of the reflected light from the surface of the inspected substrate irradiated by the linearly polarized light; a setting unit for setting a plurality of conditions in at least one of an illumination condition in the illumination unit and an imaging condition in the imaging unit; and an information processing unit for calculating a signal intensity for each portion of each of a plurality of images of the inspected substrate photographed by the imaging unit under the plurality of inspection conditions, comparing the signal intensity of the same portions in the plurality of images of the inspected substrate, and generating inspection information of the inspected substrate from information of the portions having the smallest signal intensity.

In the surface inspection apparatus described above, the signal intensity is preferably a signal intensity standardized according to the signal intensity from a normal repeating pattern.

The surface inspection apparatus described above preferably comprises a display unit for generating an inspection image on the basis of the inspection information generated by the information processing unit and visibly displaying the inspection image.

The surface inspection apparatus described above preferably comprises an inspection unit for inspecting for the presence of a defect in the repeating pattern; wherein the inspection unit is configured so as to inspect for the presence of a defect in the repeating pattern by comparing the inspection information and predetermined reference information; the illumination unit irradiates linearly polarized light to a surface of a reference substrate as a reference for the inspection under the plurality of inspection conditions, and the imaging unit captures an image of the reference substrate formed by polarization components having an oscillation direction that is different from that of the linearly polarized light as part of the reflected light from the surface of the reference substrate irradiated by the linearly polarized light; and the information processing unit calculates a signal intensity for each portion of each of the plurality of images of the reference substrate photographed by the imaging unit under the plurality of inspection conditions, compares the signal intensity of the same portions in the plurality of images of the reference substrate, extracts a portion having the smallest signal intensity for each of the portions, and generates the reference information from information of the extracted portion.

In the surface inspection apparatus described above, the inspection condition set by the setting unit is preferably an angle formed by the oscillation direction of the linearly polarized light and the oscillation direction of the polarization components.

In the surface inspection apparatus described above, the inspection condition set by the setting unit is preferably an angle formed by the repetition direction of the repeating pattern and the oscillation direction of the linearly polarized light on the surface of the inspected substrate.

In the surface inspection apparatus described above, the inspection condition set by the setting unit is preferably the wavelength of the linearly polarized light.

The surface inspection method of the present invention comprises a first step of setting an inspection condition; a second step of irradiating linearly polarized light onto a surface of an inspected substrate having a predetermined repeating pattern; a third step of capturing an image of the inspected substrate formed by polarization components having an oscillation direction that is different from that of the linearly polarized light as part of the reflected light from the surface of the inspected substrate irradiated by the linearly polarized light; and a fourth step of calculating a signal intensity for each portion of each of a plurality of images of the inspected substrate photographed under the plurality of inspection conditions in the third step, comparing the signal intensity of the same portions in the plurality of images of the inspected substrate, and generating inspection information of the inspected substrate from information of the portions having the smallest signal intensity.

The surface inspection method described above preferably comprises a fifth step of generating an inspection image on the basis of the inspection information generated in the fourth step and visibly displaying the inspection image.

The surface inspection method described above preferably comprises a sixth step of inspecting for the presence of a defect in the repeating pattern on the basis of the inspection information generated in the fourth step, the sixth step comprising inspecting for the presence of a defect in the repeating pattern by comparing the inspection information and predetermined reference information; a seventh step of irradiating linearly polarized light onto a surface of a reference substrate as a reference for the inspection under the plurality of inspection conditions; an eighth step of capturing an image of the reference substrate formed by polarization components having an oscillation direction that is different from that of the linearly polarized light as part of the reflected light from the surface of the reference substrate irradiated by the linearly polarized light under the plurality of inspection conditions; and a ninth step of calculating a signal intensity for each portion of each of the plurality of images of the reference substrate photographed under the plurality of inspection conditions in the eighth step, comparing the signal intensity of the same portions in the plurality of images of the reference substrate to extract the portions having the smallest signal intensity for each of the portions, and generating the reference information from information of the extracted portions.

In the surface inspection method described above, the inspection condition set in the first step is preferably an angle formed by the oscillation direction of the linearly polarized light and the oscillation direction of the polarization components.

In the surface inspection method described above, the inspection condition set in the first step is preferably an angle formed by the repetition direction of the repeating pattern and the oscillation direction of the linearly polarized light on the surface of the inspected substrate.

In the surface inspection method described above, the inspection condition set in the first step is preferably the wavelength of the linearly polarized light.

Advantageous Effects of the Invention

The present invention enables inspection at higher speed and accuracy.

EXPLANATION OF NUMERALS AND CHARACTERS

1: surface inspection apparatus
10: wafer (inspected substrate)
12: repeated pattern
30: illumination optical system (illumination unit)
40: imaging optical system (imaging unit)
50: image-processing apparatus (image processing unit, display unit, and inspection unit)
55: control apparatus (setting unit)
L: linearly polarized light

DESCRIPTION OF THE PREFERRED EMBODIMENTS

Figure 1:
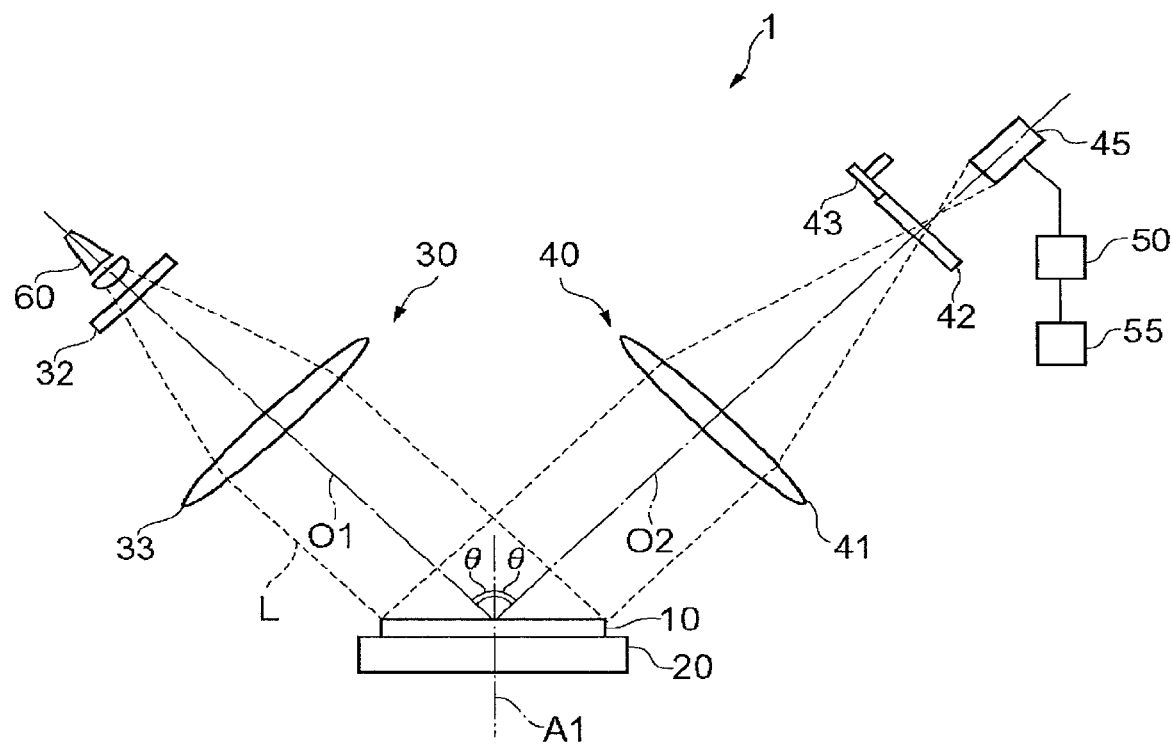
FIG. 1 is a view showing the overall structure of the surface inspection apparatus according to the present invention.

Preferred embodiments of the present invention will be described with reference to the drawings. As shown in FIG. 1, the surface inspection apparatus 1 according to the present embodiment is composed primarily of a stage 20 for supporting a semiconductor wafer 10 (hereinafter abbreviated as wafer 10) as the substrate under inspection, an illumination optical system 30, an imaging optical system 40, an image-processing apparatus 50, and a control apparatus 55. The surface inspection apparatus 1 is an apparatus for automatically inspecting a surface of the wafer 10 in the process of manufacturing a semiconductor circuit element. The wafer 10 is transported from a wafer set or development apparatus (not shown in the drawing) by a conveyance system (not shown in the drawing) after exposure/development of a resist film forming the topmost layer, and the wafer 10 is retained on the stage 20 by suction.

Figure 2:
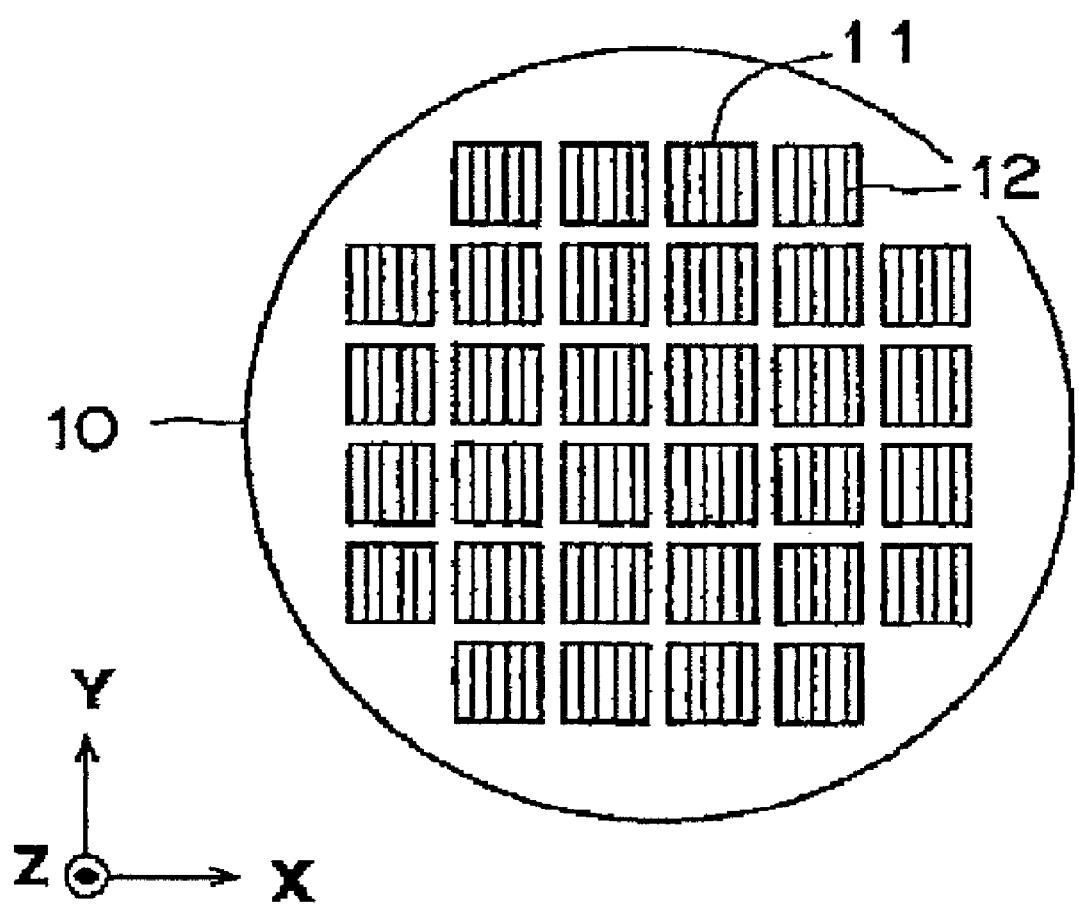
FIG. 2 is a view showing the appearance of the surface of the semiconductor wafer.
Figure 3:
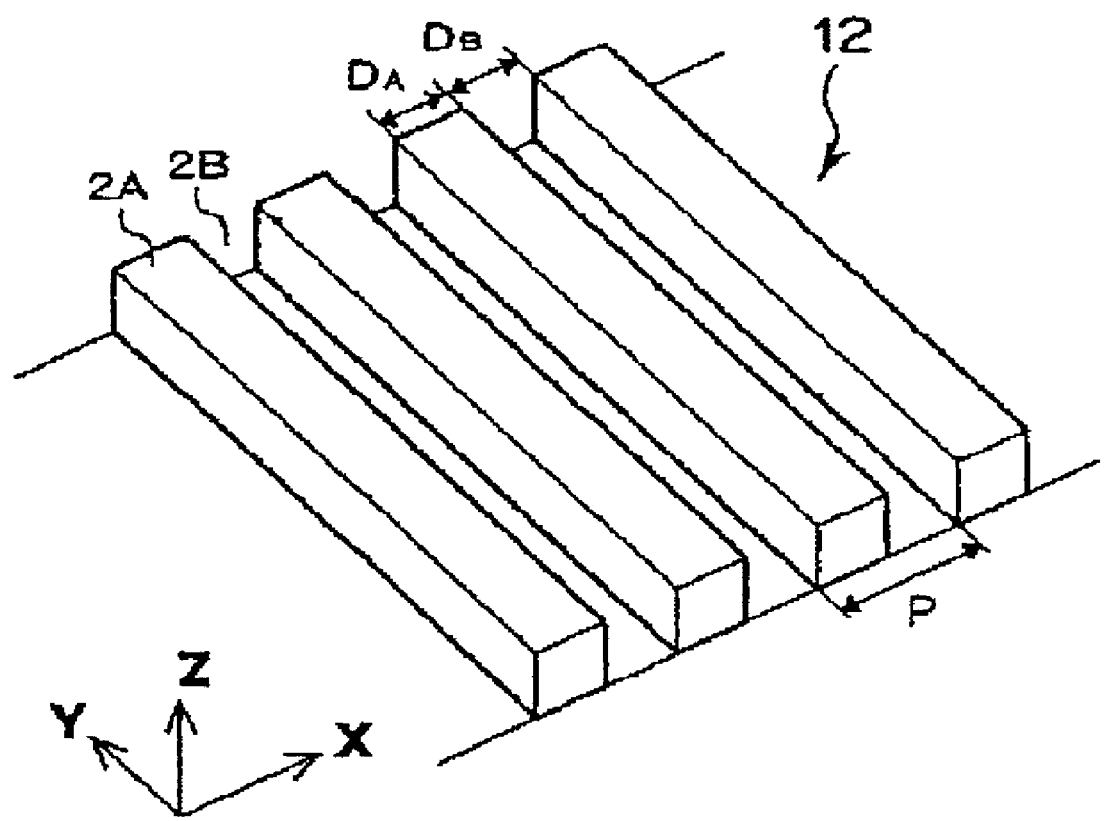
FIG. 3 is a perspective view showing the irregular structure of the repeating pattern.

On the surface of the wafer 10, a plurality of chip regions 11 is arranged in the X and Y directions, and a predetermined repeating pattern 12 is formed in each of the chip regions, as shown in FIG. 2. As shown in FIG. 3, the repeating pattern 12 is, e.g., a resist pattern (e.g., wiring pattern), in which a plurality of line portions 2A is arranged at a constant pitch P in the minor-axis direction (X direction) thereof. Space portions 2B occur between adjacent line portions 2A. The arrangement direction (X direction) of the line portions 2A is referred to as the "repetition direction of the repeating pattern 12."

Here, the line width $D_A$ of the line portions 2A in the repeating pattern 12 is set to a value ½ the pitch P. Specifically, the repeating pattern 12 has an irregular shape in which line portions 2A and space portions 2B are alternately arranged in the X direction, and when exposed at the proper exposure focus, the pattern edges are sharply formed. In the case of such an ideal shape, the luminance (signal intensity) of the polarization components detected by the imaging optical system 40 described hereinafter is maximized. However, when the exposure focus is not at the proper value, pattern breakdown occurs, and the luminance of the polarization components at this time is reduced relative to the ideal case.

The surface inspection apparatus 1 of the present embodiment performs defect inspection (PER inspection) of the repeating pattern 12 by utilizing luminance variations (variations in signal intensity) in the repeating pattern 12 such as described above, i.e., variations in the polarization state due to structural birefringence of the pattern. As described above, luminance variations are caused by a discrepancy of the exposure focus from the proper state, and occur in each shot region of the wafer 10.

In the present embodiment, the pitch P of the repeating pattern 12 is set adequately small in relation to the wavelength of the illuminating light (linearly polarized light described hereinafter) directed to the repeating pattern 12. Diffracted light from the repeating pattern 12 is therefore not created, and cannot be used to inspect the repeating pattern 12 for defects.

The stage 20 of the surface inspection apparatus 1 supports the wafer 10 on the top surface thereof, and fixes the wafer 10 in place, e.g., by vacuum suction. The stage 20 is also capable of rotating about a normal A1 as a rotational axis in the center of the top surface of the stage. This rotation mechanism enables the repetition direction (X direction in FIGS. 2 and 3) of the repeating pattern 12 in the wafer 10 to be rotated on the surface of the wafer 10.

In the present embodiment, in order to maximize the reflectance of defect inspection for the repeating pattern 12, the repetition direction of the repeating pattern 12 in the wafer 10 is set to an angle of 45° with respect to the oscillation direction of the illuminating light (linearly polarized light L) on the surface of the wafer 10. This angle is not limited to 45°, and may be set to 22.5°, 67.5°, or any other angle direction.

Figure 5:
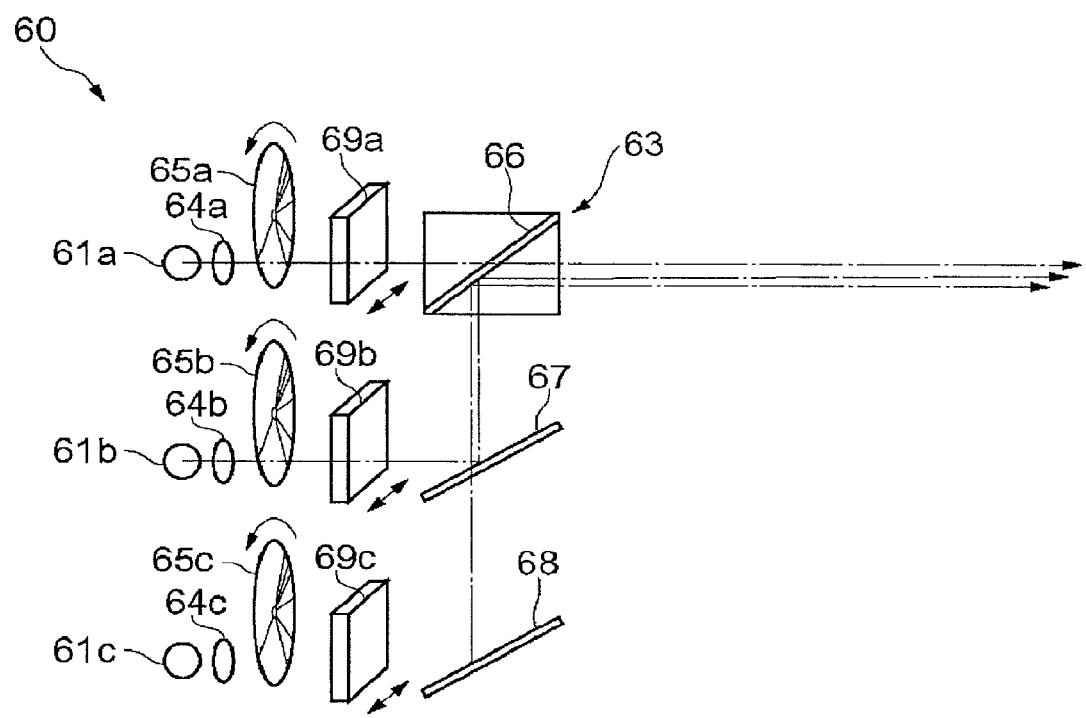
FIG. 5 is a schematic view showing the illumination apparatus.

As shown in FIG. 1, the illumination optical system 30 is composed of an illumination apparatus 60 for emitting light at a specific wavelength, a first polarizing plate 32, and a first lens 33. As shown in FIG. 5, the illumination apparatus 60 is composed of three illuminators 61a, 61b, 61c for emitting light having mutually different wavelengths, and a collecting optical system 63 for directing the light emitted from each of the illuminators 61a, 61b, 61c to the wafer 10. The first illuminator 61a is not shown in detail in the drawings, but is composed of a xenon lamp, mercury lamp, or other light source; an interference filter (band-pass filter) for extracting a desired wavelength component (bright-line spectrum) from the light from the light source, and other components, and the first illuminator 61a is configured so as to emit light having a wavelength of 546 nm (e-line).

The second illuminator 61b has the same structure as the first illuminator 61a, but is configured so as to emit light having a wavelength of 436 nm (g-line). The third illuminator 61c also has the same structure as the first illuminator 61a, but is configured so as to emit light having a wavelength of 405 nm (h-line). The three illuminators 61a, 61b, 61c each actually emit light in wavelength regions ±10 nm to ±30 nm from the aforementioned wavelengths.

The collecting optical system 63 is composed of three collective lenses 64a, 64b, 64c, three neutral density filters 65a, 65b, 65c, and three mirrors 66, 67, 68. The first collective lens 64a collects the light emitted from the first illuminator 61a and directs the light to the first neutral density filter 65a. The second and third collective lenses 64b, 64c collect the light emitted from the second and third illuminators 61b, 61c, respectively, and direct the light to the second and third neutral density filters 65b, 65c, in the same manner as the first collective lens 64a.

The first neutral density filter 65a is formed having a disk shape in which the transmittance continuously varies in the circumferential direction, and the light from the first collective lens 64a is transmitted by the first neutral density filter 65a to the first mirror 66. The first neutral density filter 65a is configured so as to be rotatable in the circumferential direction by a rotary drive apparatus not shown in the drawing, and the quantity of light emitted from the first illuminator 61a is adjusted in accordance with the rotation angle of the first neutral density filter 65a. The second and third neutral density filters 65b, 65c also have the same structure as the first neutral density filter 65a, and the light from the second and third collective lenses 64b, 64c is transmitted by the second and third neutral density filters 65b, 65c, respectively, to the second and third mirror 67, 68. The quantity of light emitted from the second and third illuminators 61b, 61c is also adjusted in accordance with the rotation angle of the second and third neutral density filters 65b, 65c, respectively.

A first shutter 69a is provided between the first neutral density filter 65a and the first mirror 66 so as to be insertable into and removable from the optical path, and is configured so that illumination by the first illuminator 61a can be switched on and off. A second shutter 69b is provided between the second neutral density filter 65b and the second mirror 67 so as to be insertable into and removable from the optical path, and is configured so that illumination by the second illuminator 61b can be switched on and off. A third shutter 69c is provided between the third neutral density filter 65c and the third mirror 68 so as to be insertable into and removable from the optical path, and is configured so that illumination by the third illuminator 61c can be switched on and off.

The third mirror 68 is a normal reflective mirror. The light from the third neutral density filter 65c is reflected toward the second mirror 67 by the third mirror 68. The second mirror 67 is a so-called dichroic mirror. The light from the second neutral density filter 65b is reflected toward the first mirror 66 by the second mirror 67, and the light from the third neutral density filter 65c is transmitted by the second mirror 67 toward the first mirror 66.

The first mirror 66 is also a so-called dichroic mirror. The light from the first neutral density filter 65a is transmitted by the first mirror 66 toward the surface of the wafer 10, and the light from the second mirror 67 is reflected by the first mirror 66 toward the surface of the wafer 10. Through this configuration, by opening any one of the first through third shutters 69a through 69c, any one of the beams from the first through third illuminators 61a through 61c (i.e., light having a wavelength of 546 nm (e-line), 436 nm (g-line) or 405 nm (h-line)) can be selectively emitted toward the wafer 10. By opening a plurality of shutters, the light from (any of) the first through third illuminators 61a through 61c can be synthesized and emitted to the wafer 10.

The first polarizing plate 32 is disposed on the optical path between the illumination apparatus 60 and the first lens 33, and converts the light emitted from the illumination apparatus 60 into linearly polarized light L (see FIG. 4) in accordance with the orientation of the transmission axis thereof. The first lens 33 converts the illumination light from the first polarizing plate 32 to a parallel luminous flux which is irradiated to the wafer 10 that is the inspected substrate. Specifically, the illumination optical system 30 is a telecentric optical system with respect to the wafer 10 side. The optical axis O1 of the illumination optical system 30 is at an angle θ with respect to the normal A1 to the stage 20.

In the illumination optical system 30 described above, the light from the illumination apparatus 60 is converted to p-polarized linearly polarized light L via the first polarizing plate 32 and the first lens 33, and is incident as illumination light on the entire surface of the wafer 10. Since the propagation direction (direction of the principal ray of the linearly polarized light L reaching any point on the surface of the wafer 10) of the linearly polarized light at this time is substantially parallel to the optical axis O1, the incident angle of the linearly polarized light L is the same at each point of the wafer 10, since the light is a parallel luminous flux, and the incident angle corresponds to the angle θ between the optical axis O1 and the normal A1.

Figure 4:
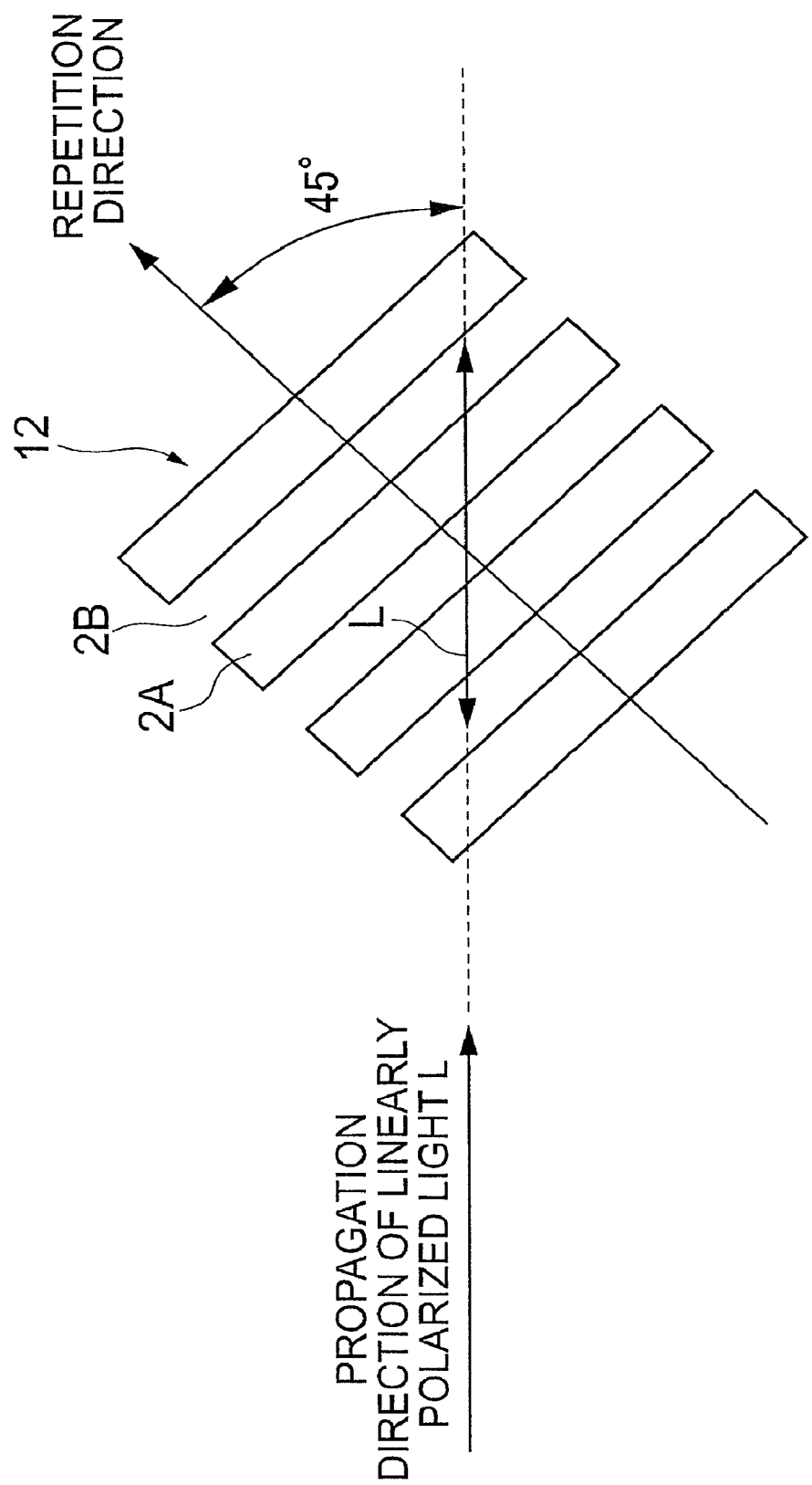
FIG. 4 is a view showing the state of inclination between the plane of incidence of the linearly polarized light and the repetition direction of the repeating pattern.

In the present embodiment, since the linearly polarized light L incident on the wafer 10 is p-polarized light, in a case in which the repetition direction of the repeating pattern 12 is set to an angle of 45° with respect to the incident plane (propagation direction of the linearly polarized light L at the surface of the wafer 10) of the linearly polarized light L as shown in FIG. 4, for example, the angle formed by the repetition direction of the repeating pattern 12 and the oscillation direction of the linearly polarized light L at the surface of the wafer 10 is also set to 45°. In other words, the linearly polarized light L is incident on the repeating pattern 12 so as to traverse the repeating pattern 12 at an angle in a state in which the oscillation direction of the linearly polarized light L at the surface of the wafer 10 is at a 45° angle to the repetition direction of the repeating pattern 12.

As shown in FIG. 1, the imaging optical system 40 is composed of a second lens 41, a second polarizing plate 42, and an imaging apparatus 45, and is disposed so that the optical axis O2 thereof is at an angle θ with respect to the normal A1 through the center of the stage 20. Consequently, direct reflection light directly reflected by the surface (repeating pattern 12) of the wafer 10 propagates along the optical axis O2 of the imaging optical system 40. The second lens 41 collects the direct reflection light toward the imaging apparatus 45, the direct reflection light having been directly reflected by the surface of the wafer 10. The direct reflection light from the wafer 10 thereby reaches the imaging surface of the imaging apparatus 45 via the second lens 41 and the second polarizing plate 42, and an image of the wafer 10 is formed.

The second polarizing plate 42 is disposed on the optical path between a second lens 41 and the imaging apparatus 45, the azimuth of the transmission axis thereof (the polarization direction) can be rotated about the optical axis of the imaging optical system 40 by using a rotary drive apparatus 43, and the azimuth of the transmission axis of the second polarizing plate 42 is set so as to be tilted at an angle about 90° from the transmission axis of the first polarizing plate 32. Consequently, (substantially right-angled) polarization components having an oscillation direction that is different from that of the linearly polarized light L as part of the direct reflection light from the wafer 10 (repeating pattern 12) can be extracted by the second polarizing plate 42 and directed to the imaging apparatus 45. As a result, a reflection image of the wafer 10 formed by (substantially right-angled) polarization components having an oscillation direction that is different from that of the linearly polarized light L as part of the direct reflection light from the wafer 10 is formed on the imaging surface of the imaging apparatus 45.

The imaging apparatus 45 is composed of a CCD picture device or the like, for example, which photoelectrically converts the reflection image of the wafer 10 formed on the imaging surface and outputs an image signal to the image-processing apparatus 50. The brightness or darkness of the reflection image of the wafer 10 is substantially proportional to the signal intensity (luminance) of the polarization components detected by the imaging apparatus 45, and varies in accordance with the shape of the repeating pattern 12. The reflection image of the wafer 10 is brightest in a case in which the repeating pattern 12 is ideally shaped.

The image-processing apparatus 50 acquires the reflection image of the wafer 10 on the basis of the image signal outputted from the imaging apparatus 45. A reflection image of a good wafer is stored in advance in the image-processing apparatus 50 for comparison. A good wafer is one in which the repeating pattern 12 is ideally formed or considered to be of ideal shape on the entire surface of the wafer. The luminance information (signal intensity) of the reflection image of a good wafer is therefore considered to exhibit the highest luminance value.

Consequently, when the image-processing apparatus 50 acquires the reflection image of the wafer 10 functioning as the inspected substrate, the image-processing apparatus 50 compares the luminance information (signal intensity) thereof with the luminance information (signal intensity) of the reflection image of the good wafer. A defect in the repeating pattern 12 is detected on the basis of the amount by which the luminance value of a dark location is reduced in the reflection image of the wafer 10. For example, a determination of "defective" is made when the luminance variation is greater than a predetermined threshold value (allowable value), and a determination of "normal" is made when the luminance variation is smaller than the threshold value. The result of comparing the luminance information (signal intensity) by the image-processing apparatus 50 and the reflection image of the wafer 10 at that time are visibly displayed by a monitor unit of the image-processing apparatus 50. The control apparatus 55 controls operations in general for the stage 20, the illumination apparatus 60, the rotary drive apparatus 43 of the second polarizing plate 42, the image-processing apparatus 50, and other components.

The image-processing apparatus 50 may be configured so as to store a reflection image of a good wafer in advance, as described above, or may be configured so as to store a luminance threshold value and arrangement data for a shot region of the wafer 10. In this case, the position of each shot region in the acquired reflection image of the wafer 10 is known based on the arrangement data of the shot regions, and the luminance value of each shot region can therefore be calculated. Defects in the pattern are then detected by comparing the luminance value with the stored threshold value. A shot region in which the luminance value is smaller than the threshold value triggers a determination of "defective."

Figure 6:
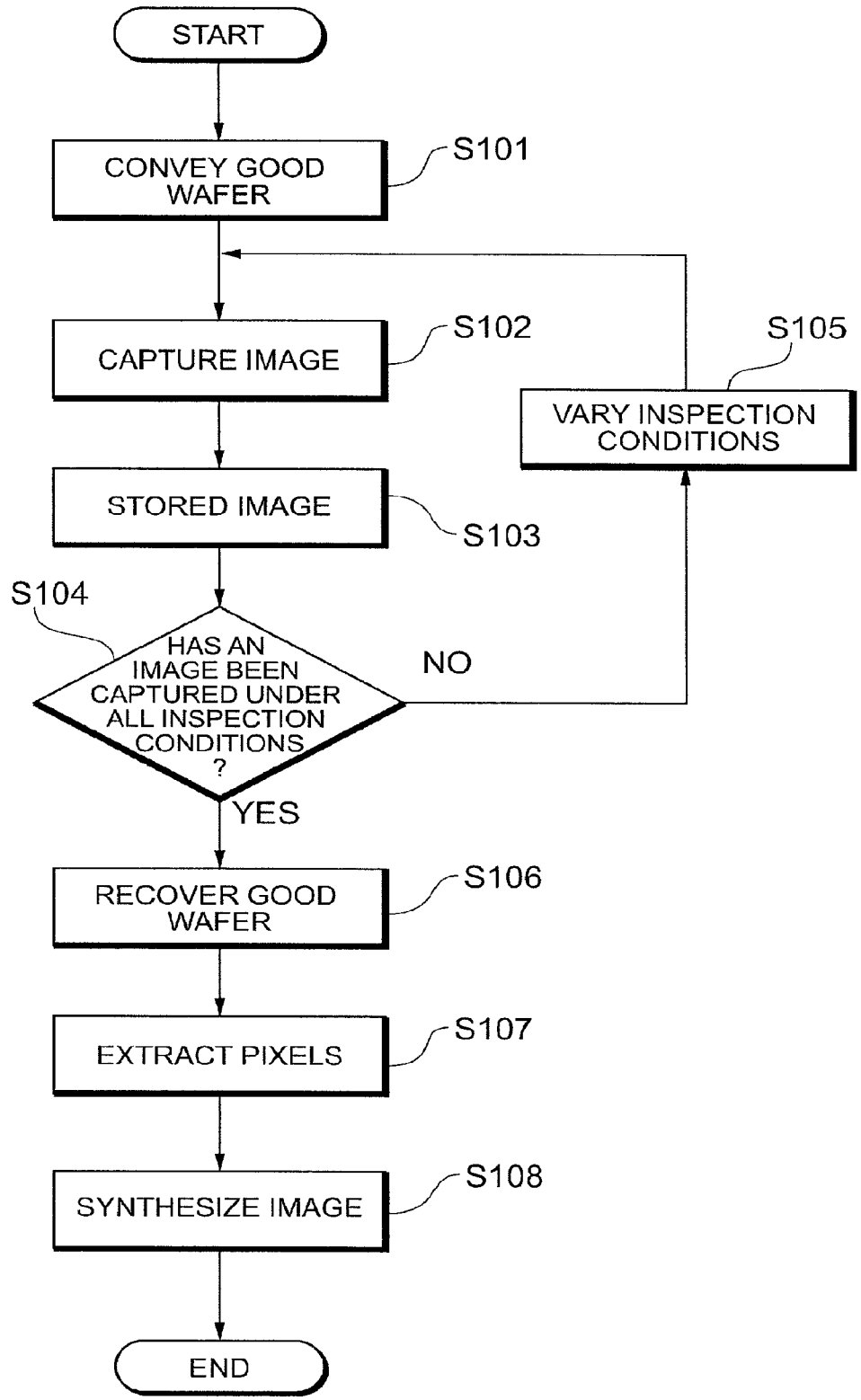
FIG. 6 is a first flowchart showing the surface inspection method according to the present invention.

A surface inspection method using the surface inspection apparatus 1 configured as described above will be described with reference to the flowcharts shown in FIGS. 6 and 7. The step of generating a reference image of a good wafer (not shown) performed at the time of recipe creation will first be described using the flowchart shown in FIG. 6. First, in step S101, a good wafer is conveyed onto the stage 20 and positioned with respect to the repeating pattern on the good wafer. The control apparatus 55 at this time controls driving of the stage 20 so that the azimuth angle (angle formed by the oscillation direction of the linearly polarized light L on the surface of the wafer and the repetition direction of the repeating pattern) of the pattern with respect to the oscillation direction of the linearly polarized light L matches the predetermined azimuth angle (of the initial setting). The control apparatus 55 also controls driving of the rotary drive apparatus 43 at this time so that the bearing of the transmission axis of the second polarizing plate 42 with respect to the transmission axis of the first polarizing plate 32 is at the predetermined angle of inclination (of the initial setting). Also at this time, the control apparatus 55 controls the operation of the first through third shutters 69a through 69c so that the wavelength of the light emitted from the illumination apparatus 60 is a prescribed wavelength (of the initial setting).

When the inspection conditions have thus been set, the linearly polarized light L is irradiated onto the surface of the good wafer, and an image of the good wafer is captured in the next step S102, the image being formed by polarization components having an oscillation direction at substantially a right angle to the linearly polarized light L as part of the direct reflection light from the surface of the good wafer. At this time, the light emitted from the illumination apparatus 60 is converted to p-polarized linearly polarized light L by the first polarizing plate 32, converted to a parallel luminous flux by the first lens 33, and irradiated onto the surface of the good wafer. The direct reflection light reflected by the surface of the good wafer is collected by the second lens 41, and polarization components having an oscillation direction at a substantially right angle to the linearly polarized light L as part of the direct reflection light are extracted by the second polarizing plate 42 and directed onto the imaging surface of the imaging apparatus 45. The imaging apparatus 45 then photoelectrically converts the reflection image of the good wafer formed by the polarization components having an oscillation direction at substantially a right angle to the linearly polarized light L as part of the direct reflection light, and outputs an image signal to the image-processing apparatus 50.

When the image signal is outputted to the image-processing apparatus 50 from the imaging apparatus 45, in the next step S103, the image-processing apparatus 50 acquires the reflection image of the good wafer on the basis of the image signal outputted from the imaging apparatus 45 and stores image data of the good wafer in an internal memory (not shown) of the image-processing apparatus 50.

In the next step S104, a determination is made as to whether the good wafer was photographed under all the necessary inspection conditions. In a case in which the determination is "No," after step S105 is performed, steps S102 and S103 are repeated under the inspection conditions in which an image had not yet been captured. In a case in which the determination is "Yes," the process proceeds to step S106.

The inspection conditions determined in step S104 are the three parameters of the azimuth angle of the pattern, the angle of inclination of the second polarizing plate 42, and the illumination wavelength. Specifically, an image of the good wafer is captured for each set of inspection conditions made up of combinations of the three parameters. Therefore, processing takes place in step S105 whereby the control apparatus 55 changes the setting of at least one of the three types of parameters in the inspection conditions. At this time, any azimuth angle selected from, e.g., 45°, 67.5°, and 22.5° is set as the azimuth angle of the pattern. This is because the condition (azimuth angle) under which the detection sensitivity increases with respect to defocusing varies according to the type of pattern (e.g., memory circuit pattern or logic circuit pattern). Azimuth angles of 135°, 157.5°, and 112.5° may be further added.

The inclination angle of the second polarizing plate 42 is set at a 0.5° pitch in a range of 90° (crossed Nicols state) ±4°. This is because in defect inspection (PER inspection) of the type performed in the present embodiment, although the detection sensitivity with respect to defocusing has been found to increase when the inclination angle of the second polarizing plate 42 is slightly offset from 90° (crossed Nicols state), the condition for increasing the detection sensitivity varies according to the semiconductor process. The illumination wavelength is set to any of 546 nm (e-line), 436 nm (g-line) and 405 nm (h-line). This is also for the reason that the condition for increasing the detection sensitivity varies according to the semiconductor process. However, since unevenness due to interference with the base of the pattern can occur at some illumination wavelengths, such illumination wavelength conditions are excluded from the inspection conditions in advance. Since unevenness due to interference with the base of the pattern also sometimes occurs under some conditions irrespective of the illumination wavelength, conditions that produce such anomalies are also excluded.

The quantity of illumination light is also adjusted by the first through third neutral density filters 65a through 65c in each inspection condition so that the luminance value (signal intensity) of the portion used as a reference in the image of the good wafer captured in step S102 is constant. At this time, the control apparatus 55 controls driving of the rotary drive apparatuses (not shown) of the first through third neutral density filters 65a through 65c so that the luminance value (signal intensity) of the portion used as a reference in the image of the good wafer is constant, or in other words, so that standardization is obtained according to the luminance value (signal intensity) of the portion (repeating pattern) used as a reference in the image of the good wafer. The gain in the image-processing apparatus 50 may also be adjusted instead of adjusting the quantity of light through the use of the first through third neutral density filters 65a through 65c.

In step S106, the good wafer which has been photographed under a plurality of inspection conditions is unloaded and recovered from the stage 20, and in the next step S107, the image-processing apparatus 50 compares pixels in the same pixel position in the images of the good wafer photographed under a plurality of conditions, extracts each of the pixels (of the inspection conditions) having the smallest luminance value (signal intensity), and sets the current luminance value (signal intensity) as the luminance value (true value) for the corresponding pixel position.

In the next step S108, the image-processing apparatus 50 generates a single reference image by connecting the pixels having the smallest luminance values (signal intensities) on the basis of the luminance value (signal intensity) of each pixel set in step S107. A reference image of the time of wafer inspection is thereby generated as an image of the good wafer, and the reference image of the good wafer is stored in the internal memory of the image-processing apparatus 50. In step S108, in a case in which the process is changed, such as when the material of the resist film changes in the same type of pattern, the same processing as in steps S101 through S107 is performed for a good wafer exposed/developed by the new process, and additional study can be performed for replacing pixels whose luminance values (true values) have become relatively brighter by comparison with the reference image of the good wafer stored in the internal memory.

Figure 7:
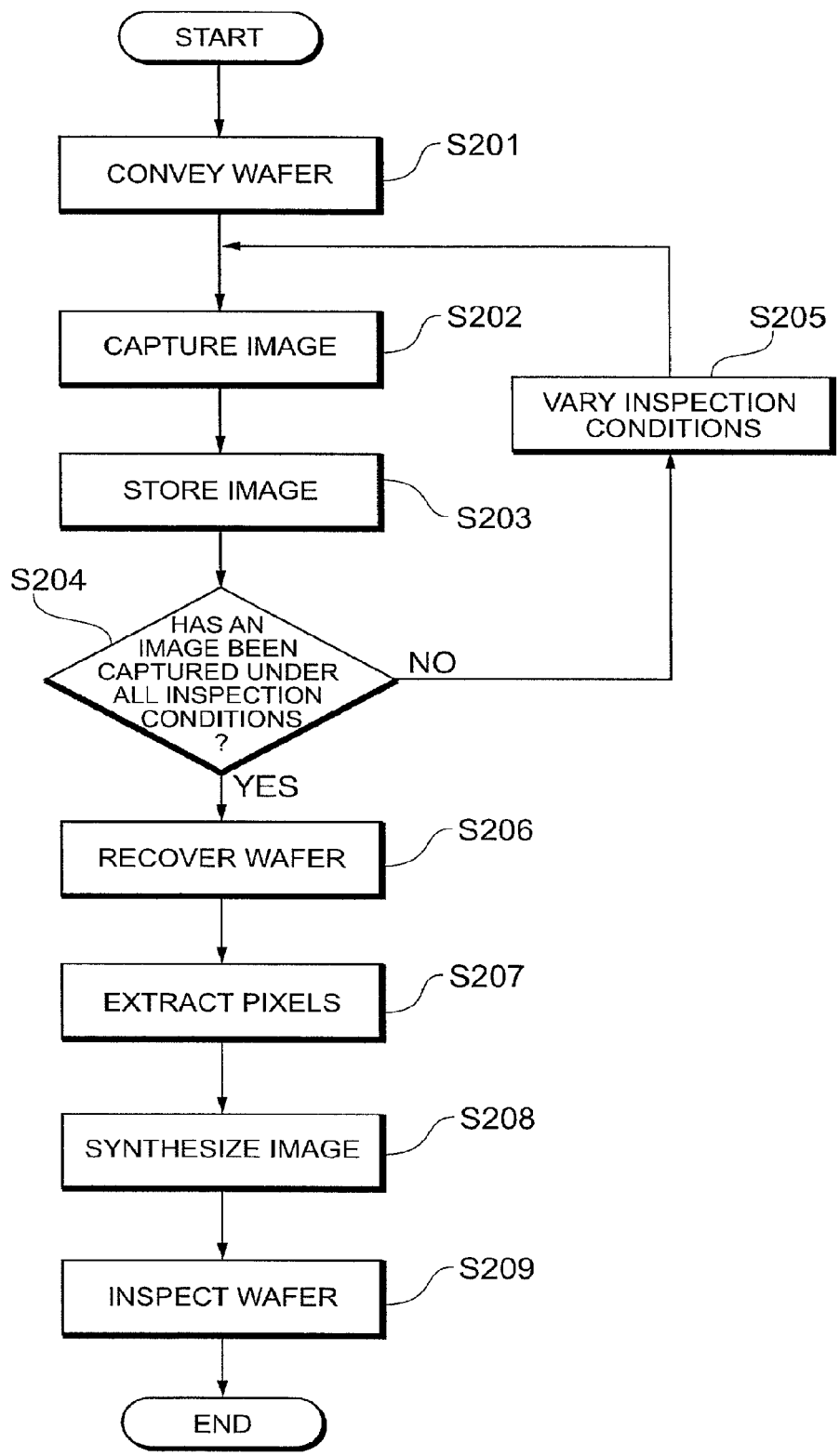
FIG. 7 is a second flowchart showing the surface inspection method according to the present invention.

The flowchart shown in FIG. 7 will next be used to describe the process for inspecting the wafer 10. First, in step S201, the wafer 10 as the inspected substrate is conveyed onto the stage 20 and positioned with respect to the repeating pattern 12 on the wafer 10. The control apparatus 55 at this time controls driving of the stage 20 so that the azimuth angle of the pattern matches the predetermined azimuth angle (of the initial setting), under the same conditions as in the case of generating the reference image of the good wafer. The control apparatus 55 also controls driving of the rotary drive apparatus 43 so that the inclination angle of the second polarizing plate 42 is at the predetermined inclination angle (of the initial setting), and the control apparatus 55 controls the operation of the first through third shutters 69a through 69c so that the illumination wavelength is the predetermined wavelength (of the initial setting).

When the inspection conditions have thus been set, the linearly polarized light L is irradiated onto the surface of the wafer 10, and an image of the wafer 10 is captured in the next step S202, the image being formed by polarization components having an oscillation direction at substantially a right angle to the linearly polarized light L as part of the direct reflection light from the surface of the wafer 10. At this time, the light emitted from the illumination apparatus 60 is converted to p-polarized linearly polarized light L by the first polarizing plate 32, converted to a parallel luminous flux by the first lens 33, and irradiated onto the surface of the wafer 10. The direct reflection light reflected by the surface of the wafer 10 is collected by the second lens 41, and polarization components having an oscillation direction at a substantially right angle to the linearly polarized light L as part of the direct reflection light are extracted by the second polarizing plate 42 and directed onto the imaging surface of the imaging apparatus 45. The imaging apparatus 45 then photoelectrically converts the reflection image of the wafer 10 formed by the polarization components having an oscillation direction at substantially a right angle to the linearly polarized light L as part of the direct reflection light, and outputs an image signal to the image-processing apparatus 50.

When the image signal is outputted to the image-processing apparatus 50 from the imaging apparatus 45, in the next step S203, the image-processing apparatus 50 acquires the reflection image of the wafer 10 on the basis of the image signal outputted from the imaging apparatus 45 and stores image data of the wafer 10 in an internal memory (not shown) of the image-processing apparatus 50.

In the next step S204, a determination is made as to whether the wafer 10 was photographed under all the necessary inspection conditions. In a case in which the determination is "No," after step S205 is performed, steps S202 and S203 are repeated under the inspection conditions in which an image had not yet been captured. In a case in which the determination is "Yes," the process proceeds to step S206.

The inspection conditions determined in step S204 are the same as those under which the reference image of the good wafer was generated. Specifically, as many images of the wafer 10 are captured as the number of inspection conditions that are the same as those of the case in which the reference image of the good wafer was generated. Therefore, processing takes place in step S205 whereby the control apparatus 55 changes the setting of at least one of the three types of parameters (azimuth angle of the pattern, inclination angle of the second polarizing plate 42, and illumination wavelength) in the inspection conditions. The quantity of illumination light is also adjusted by the first through third neutral density filters 65a through 65c under the same conditions as when the reference image of the good wafer was generated.

In step S206, the wafer 10 which has been photographed under a plurality of inspection conditions is unloaded and recovered from the stage 20, and in the next step S207, the image-processing apparatus 50 compares pixels in the same pixel position in the images of the wafer 10 photographed under a plurality of conditions, extracts each pixel (of the inspection conditions) having the smallest luminance value (signal intensity), and sets the current luminance value (signal intensity) as the luminance value (true value) for the corresponding pixel position.

In the next step S208, the image-processing apparatus 50 generates a single inspection image by connecting the pixels having the smallest luminance values (signal intensities) on the basis of the luminance value (signal intensity) of each pixel set in step S207. An inspection image of the wafer 10 is thereby generated, and the inspection image of the wafer 10 is stored in the internal memory of the image-processing apparatus 50.

In the next step S209, the image-processing apparatus 50 compares the luminance information (i.e., inspection information) of the inspection image of the wafer 10 generated in step S208 with the luminance information (i.e., reference information) of the reference image of the good wafer generated previously in step S108, and determines that a defect is present when the luminance variation exceeds a pre-set threshold value. At this time, the result of comparing the luminance information (signal intensity) by the image-processing apparatus 50 and the reflection image (inspection image) of the wafer 10 at that time are visibly displayed by a monitor unit of the image-processing apparatus 50, and visual inspection is also made possible.

As a result, through the surface inspection apparatus 1 and surface inspection method of the present embodiment, since the luminance information (signal intensity) of the image of the good wafer is considered to exhibit the highest luminance value in defect inspection (PER inspection) such as that of the present embodiment, highly accurate inspection at high speed and high detection sensitivity is made possible by performing inspection on the basis of an inspection image of the wafer 10 generated by extracting for each pixel of the image having the smallest luminance value (signal intensity) among the images of the wafer 10 photographed under a plurality of inspection conditions and connecting the pixels having the smallest luminance value (signal intensity), rather than conducting inspections under all inspection conditions. The luminance value in the reflection image of the wafer 10 decreases as well in cases in which exposure was not performed at the correct dose amount, but the optimum conditions for detecting dose amount defects vary according to whether the dose amount is excessive or inadequate. Thus, even for defects of the same type, the optimum conditions for detecting defects vary according to the severity of the defect. Through the present embodiment, however, since the wafer 10 is inspected based on an inspection image of the wafer 10 generated by connecting pixels having the smallest luminance value (signal intensity) among the images of the wafer 10 photographed under a plurality of inspection conditions, defects of different types or defects of the same type with different severity can all be easily recognized from a single inspection image, and inspection can be performed with high detection sensitivity and high accuracy. Inspecting a wafer on the basis of a single inspection image in this manner also shortens the image processing time for detecting defects for each shot, thus enabling high-speed inspection.

By generating the reference image of the good wafer by the same procedure as the inspection image of the wafer 10 is generated, erroneous detection of defects can be prevented, and a more highly accurate inspection can be obtained. Since the resist film of the wafer 10 decreases in thickness from the center of the wafer 10 outward, the dose amount sometimes varies according to the thickness of the resist film. In such cases, the line width or the like is sometimes increased in order to prevent the pattern from collapsing at the outside of the wafer 10 where the resist film is relatively thin, and the luminance value used as a reference in the good wafer then varies for each shot. However, by generating the reference image of the good wafer by the same procedure as the inspection image of the wafer 10, since a reference image of the good wafer is generated in which the luminance value varies for each shot, erroneous detection of defects can be prevented, and a more highly accurate inspection can be obtained.

In the embodiment described above, three types of parameters including the azimuth angle of the pattern, the inclination angle of the second polarizing plate 42, and the illumination wavelength are varied in the inspection conditions in photographing the wafer, but this configuration is not limiting; a configuration may be adopted in which the setting of only one (or two) of the three types of parameters is varied (specifically, inspection conditions may be used in which the setting of any one (or two) of the parameters including the azimuth angle of the pattern, the inclination angle of the second polarizing plate 42, and the illumination wavelength is varied).

Figure 8:
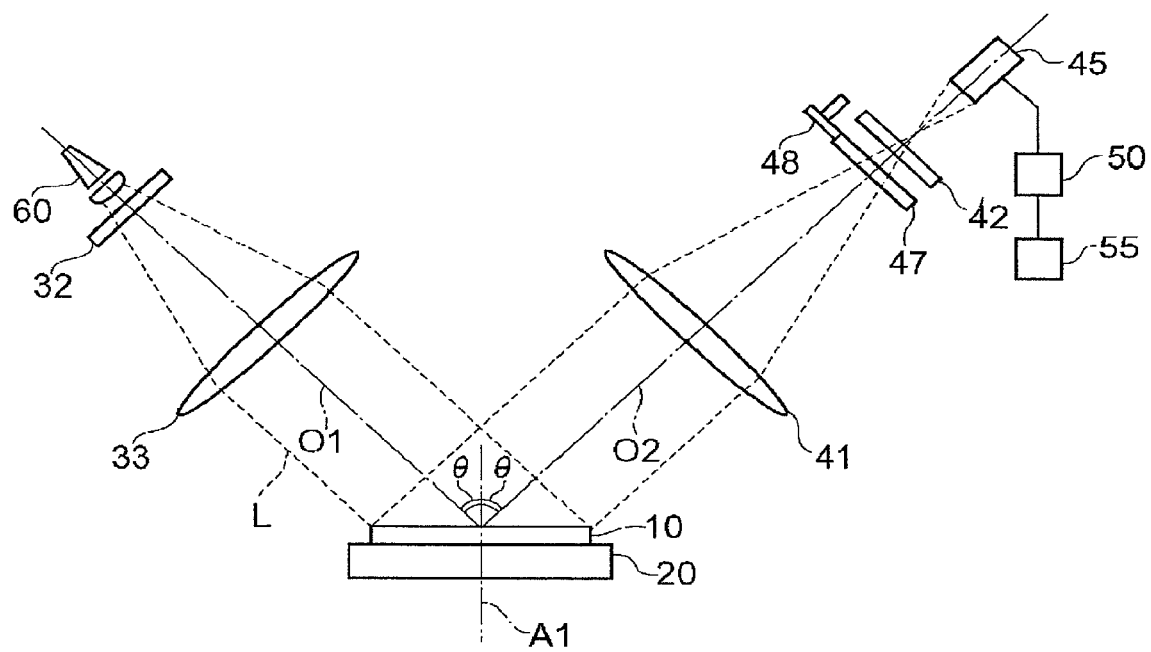
FIG. 8 is a view showing a modification of the surface inspection apparatus.

In the embodiment described above, the second polarizing plate 42 is configured so that the bearing of the transmission axis can be rotated about the optical axis O2 of the imaging optical system 40 by using the rotary drive apparatus 43, but this configuration is not limiting. For example, a configuration may be adopted in which a ½λ plate 47 is provided between the second lens 41 and the second polarizing plate 42, and the bearing of the slow axis of the ½λ plate 47 is rotated about the optical axis O2 by using a rotary drive apparatus 48, as shown in FIG. 8.

In the embodiment described above, 546 nm (e-line), 436 nm (g-line), and 405 nm (h-line) are used as the illumination wavelengths, but this configuration is not limiting; other wavelengths may also be used, such as 365 nm (i-line) and 313 nm (j-line).

In the embodiment described above, the image-processing apparatus 50 generates the inspection image of the wafer 10 and inspects for the presence of defects in the repeating pattern 12 on the basis of the generated inspection image of the wafer 10, but this configuration is not limiting; each of an image processing unit for generating an inspection image of the wafer 10, and an inspection unit for inspecting for the presence of defects in the repeating pattern 12 may be separately provided.

What is claimed is:

1. A surface inspection apparatus comprising:
   an illumination unit which irradiates linearly polarized light onto a surface of an inspection substrate having a predetermined repeating pattern;
   an imaging unit which captures an image of the inspection substrate formed by polarization components having an oscillation direction that is different from that of the linearly polarized light as part of the reflected light from the surface of the inspection substrate irradiated by the linearly polarized light;
   a setting unit which sets a plurality of inspection conditions for at least one of an illumination condition in the illumination unit and an imaging condition in the imaging unit; and
   an information processing unit which calculates respective signal intensities for portions in each of a plurality of images of the inspection substrate captured by the imaging unit under the plurality of inspection conditions, which compares the signal intensities of corresponding portions from the plurality of images of the inspection substrate, and which generates inspection information of the inspection substrate from information of a portion having a smallest signal intensity.

2. The surface inspection apparatus according to claim 1, wherein signal intensities are standardized according to a signal intensity from a normal repeating pattern.

3. The surface inspection apparatus according to claim 1, comprising a display unit which generates an inspection image based on the inspection information generated by the information processing unit and visibly displays the inspection image.

4. The surface inspection apparatus according to claim 1, comprising an inspection unit, wherein
   the inspection unit is configured to inspect for the presence of a defect in the repeating pattern by comparing the inspection information and predetermined reference information;
   the illumination unit irradiates linearly polarized light onto a surface of a reference substrate as a reference for the inspection under the plurality of inspection conditions, and the imaging unit captures an image of the reference substrate formed by polarization components having an oscillation direction that is different from that of the linearly polarized light as part of the reflected light from the surface of the reference substrate irradiated by the linearly polarized light; and
   the information processing unit calculates respective signal intensities for portions in each of a plurality of images of the reference substrate captured by the imaging unit under the plurality of inspection conditions, compares the signal intensities of corresponding portions from the plurality of images of the reference substrate, extracts a portion having the smallest signal intensity, and generates the reference information from information of the extracted portion.

5. The surface inspection apparatus according to claim 1, wherein an inspection condition set by the setting unit is an angle formed by the oscillation direction of the linearly polarized light and the oscillation direction of the polarization components.

6. The surface inspection apparatus according to claim 1, wherein an inspection condition set by the setting unit is an angle formed by the repetition direction of the repeating pattern and the oscillation direction of the linearly polarized light on the surface of the inspection substrate.

7. The surface inspection apparatus according to claim 1, wherein an inspection condition set by the setting unit is a wavelength of the linearly polarized light.

8. A surface inspection method comprising:
   setting a plurality of inspection conditions;
   irradiating linearly polarized light to a surface of an inspection substrate having a predetermined repeating pattern under each inspection condition;
   capturing an image of the inspection substrate formed by polarization components having an oscillation direction that is different from that of the linearly polarized light as part of the reflected light from the surface of the inspection substrate irradiated by the linearly polarized light under each inspection condition; and
   calculating respective signal intensities for portions in each of a plurality of images of the inspection substrate captured under the plurality of inspection conditions, comparing signal intensities in different groups of corresponding portions from the plurality of images of the inspection substrate, and generating inspection information of the inspection substrate from information of a portion having the smallest signal intensity in each group.

9. The surface inspection method according to claim 8, further comprising generating an inspection image based on the inspection information, and visibly displaying the inspection image.

10. The surface inspection method according to claim 8, further comprising:
   irradiating linearly polarized light onto a surface of a reference substrate under each inspection condition;
   capturing an image of the reference substrate formed by polarization components having an oscillation direction that is different from that of the linearly polarized light as part of the reflected light from the surface of the reference substrate irradiated by the linearly polarized light under each inspection condition;
   calculating respective signal intensities for portions in each of a plurality of images of the reference substrate captured under the plurality of inspection conditions, comparing signal intensities in different groups of corresponding portions from the plurality of images of the reference substrate to extract a portion having the smallest signal intensity in each group, and generating reference information from information of the extracted portions; and
   inspecting for the presence of a defect in the repeating pattern by comparing the inspection information and the reference information.

11. The surface inspection method according to claim 8, wherein an inspection condition set in the first step is an angle formed by the oscillation direction of the linearly polarized light and the oscillation direction of the polarization components.

12. The surface inspection method according to claim 8, wherein an inspection condition set in the first step is an angle formed by the repetition direction of the repeating pattern and the oscillation direction of the linearly polarized light on the surface of the inspection substrate.

13. The surface inspection method according to claim 8, wherein an inspection condition set in the first step is a wavelength of the linearly polarized light.

14. The surface inspection apparatus according to claim 1, wherein the information processing unit compares the signal intensities in different groups of corresponding portions from the plurality of images of the inspection substrate, and generates inspection information of the inspection substrate from information of a portion having the smallest signal intensity in each group.

15. The surface inspection apparatus according to claim 4, wherein the information processing unit compares the signal intensities in different groups of corresponding portions from the plurality of images of the reference substrate, extracts a portion having the smallest signal intensity in each group, and generates the reference information from information of the extracted portions.

* * * * *